US012332193B2

(12) United States Patent
Beckett et al.

(10) Patent No.: US 12,332,193 B2
(45) Date of Patent: Jun. 17, 2025

(54) PULSED NEUTRON APPARATUS AND METHOD FOR USING SAME TO ANALYZE CORE SAMPLES

(71) Applicant: Core Laboratories LP, Houston, TX (US)

(72) Inventors: Derek Raymond Beckett, Houston, TX (US); Grant Philip Goodyear, Houston, TX (US); Theodore Joseph Griffin, Jr., Houston, TX (US); Kent E. Newsham, Houston, TX (US); Milomir Pavlovic, Houston, TX (US); Roland Edward Chemali, Houston, TX (US)

(73) Assignee: Core Laboratories LP, Houston, TX (US)

( * ) Notice: Subject to any disclaimer, the term of this patent is extended or adjusted under 35 U.S.C. 154(b) by 0 days.

(21) Appl. No.: 17/732,144

(22) Filed: Apr. 28, 2022

(65) Prior Publication Data
US 2022/0349846 A1    Nov. 3, 2022

Related U.S. Application Data

(60) Provisional application No. 63/182,647, filed on Apr. 30, 2021.

(51) Int. Cl.
*G01N 23/046* (2018.01)
*G01N 23/083* (2018.01)
(Continued)

(52) U.S. Cl.
CPC ....... *G01N 23/2206* (2013.01); *G01N 23/046* (2013.01); *G01N 23/083* (2013.01);
(Continued)

(58) Field of Classification Search
CPC ............ G01N 23/2206; G01N 23/046; G01N 23/083; G01N 33/24; G01N 2223/04;
(Continued)

(56) References Cited

U.S. PATENT DOCUMENTS

| 4,471,435 A * | 9/1984 | Meisner ................. G01V 5/102 250/262 |
| 2009/0283690 A1* | 11/2009 | Bendahan ............ G01V 5/0033 376/159 |

(Continued)

FOREIGN PATENT DOCUMENTS

WO    2020/149983 A1    7/2020

OTHER PUBLICATIONS

Stephen "Recent advances in LWD/MWD and formation evaluation; Developments include wireline and while-drilling logging, autotuning NMR technology, radical acoustic measurements and 3D digital core-evaluation methods"; World Oil Online; Researchgate, Mar. 2006, p. 1-9 (Year: 2006).*

(Continued)

*Primary Examiner* — David P Porta
*Assistant Examiner* — Mamadou Faye
(74) *Attorney, Agent, or Firm* — Crowe & Dunlevy, P.C.

(57) ABSTRACT

An apparatus for analyzing a core sample obtained from a subterranean formation includes a neutron generator, a plurality of detectors, a computed tomography scanner, an information processing device, and a transport system. The neutron generator can operate in a pulsed mode and emit neutrons into the core sample.

20 Claims, 5 Drawing Sheets

(51) Int. Cl.
*G01N 23/2206* (2018.01)
*G01N 33/24* (2006.01)

(52) U.S. Cl.
CPC ......... *G01N 33/24* (2013.01); *G01N 2223/04* (2013.01); *G01N 2223/071* (2013.01); *G01N 2223/1063* (2013.01); *G01N 2223/1066* (2013.01); *G01N 2223/419* (2013.01); *G01N 2223/616* (2013.01)

(58) Field of Classification Search
CPC ..... G01N 2223/071; G01N 2223/1063; G01N 2223/1066; G01N 2223/419; G01N 2223/616; G01N 33/241; G01N 33/246; G01N 223/053; G01N 2223/063; G01N 2223/0745; G01N 2223/3308; G01N 23/204; G01N 23/221
See application file for complete search history.

(56) References Cited

U.S. PATENT DOCUMENTS

2012/0301004 A1* 11/2012 Kingston ............. G01N 23/046
  382/131
2016/0349398 A1   12/2016 Zhou et al.

OTHER PUBLICATIONS

ISA/US; International Search Report and Written Opinion for PCT/US2022/026806 mailed Jul. 29, 2022.
Lawrence M. Anovitz et al, "Characterization and Analysis of Porosity and Pore Structures", Reviews in Mineralogy and Geochemistry, Jan. 1, 2015, pp. 61-164, vol. 80.
"IAEA—TECDOC-537 Prompt Gamma Neutron Activation Analysis in Borehole Logging and Industrial Process Control", Jan. 1, 1990, p. 16.

* cited by examiner

PULSED NEUTRON APPARATUS AND METHOD FOR USING SAME TO ANALYZE CORE SAMPLES

BACKGROUND

Field

The present disclosure relates to core analysis equipment and methods for analyzing subterranean core samples.

Description of the Related Art

Traditionally, subsurface cores have been acquired, surfaced, and transported to a laboratory in the inner tube of a core barrel. Subsequent measurements necessitate removing the core from the inner barrel, selecting representative sampling sites, subsampling the core and finally, observing and measuring relevant properties via oft times complicated and protracted protocols. This process is time-consuming, labor-intensive and costly. The resulting data, helpful in well stimulation and completion, are rarely available for these decision-making processes. Additionally, removal of the core from the inner barrel, which serves as a hermetically sealed containment system, exposes the core to atmospheric conditions. Under such conditions, certain core characteristics and fluid saturations can change, which renders the data less representative and useful. The present disclosure addresses the need to obtain critical data rapidly, to acquire data on the entire core rather than specific sampling sites on the core sample, and to acquire data on core at more representative reservoir conditions, as well as other needs of the prior art.

SUMMARY

In aspects, the present disclosure provides an apparatus for analyzing a core sample obtained from a subterranean formation. The apparatus may include a neutron generator, a plurality of detectors, a computed tomography scanner, an information processing device, and a transport system. The neutron generator can operate in a pulsed mode and emit neutrons into the core sample. The neutrons include fast neutrons.

The plurality of detectors may include at least one gamma detector configured to estimate a gamma pulse-height spectrum that results from emitted neutrons interacting with the core sample, a plurality of fast neutron detectors generating at least a first count rate and a second count rate, the plurality of fast neutrons including at least: (i) a first fast neutron detector configured to generate the first count rate by monitoring the neutron generator output and counting the number of fast neutrons coming from the neutron generator over a period of time, and (ii) a second fast neutron detector configured to generate the second count rate by counting the number of fast neutrons that are transmitted through the core sample over the period of time, and at least one thermal neutron detector configured to generate a third count rate by counting a number of thermal neutrons over the period of time, the thermal neutrons being emitted neutrons that have been slowed down to thermal energies by passing through the core sample, and at least one epithermal neutron detector configured to generate a fourth count rate by counting a number of epithermal neutrons over the period of time, the epithermal neutrons being emitted neutrons that have been slowed down to epithermal energies by passing through the core sample but still have more energy than thermal neutrons.

The apparatus may also include a computed tomography scanner in which a conical beam of X-rays is aimed at the core sample and which may be rotated around the sample, an information processing device in signal communication with the plurality of detectors and configured to separate count events on a nanosecond time scale, and a transport system configured to allow relative movement between the core sample and the plurality of detectors and between the core sample and the neutron generator.

In aspects, the present disclosure also provides a method for analyzing a core sample obtained from a subterranean formation. The method may include generating a first information set by analyzing the core sample using the nuclear features described above, generating a second information set by analyzing the core sample using the computerized tomography scanner, and estimating a selected parameter of interest relating to the subterranean formation using the first information set and the second information set.

It should be understood that examples of certain features of the disclosure have been summarized rather broadly in order that the detailed description thereof that follows may be better understood, and in order that the contributions to the art may be appreciated. There are, of course, additional features of the disclosure that will be described hereinafter and which will in some cases form the subject of the claims appended thereto.

BRIEF DESCRIPTION OF THE DRAWINGS

For detailed understanding of the present disclosure, references should be made to the following detailed description of the preferred embodiment, taken in conjunction with the accompanying drawings, in which like elements have been given like numerals and wherein.

DETAILED DESCRIPTION

In aspects, the present disclosure provides pulsed neutron devices that may be used to analyze subterranean core samples. The pulsed neutron devices described herein furnish critical measurements heretofore not possible to be made. In certain embodiments, these measurements may be made through the inner barrel rapidly and accurately. Utilization of neutron and gamma radiation flux has been historically error susceptible and sometimes limited by vagaries in the inner barrel annular space. These vagaries may arise from core acquisition issues, core mechanical integrity and variable mud system occlusion, all of which adversely impact signal interpretation. The present teachings utilize computed tomography to define core mass, density and geometry and mud quantity by linear depth position.

Knowledge of these variables may be useful to characterize the annulus correction, and therefore to make definitive determinations of the neutron signals.

Figure 1:
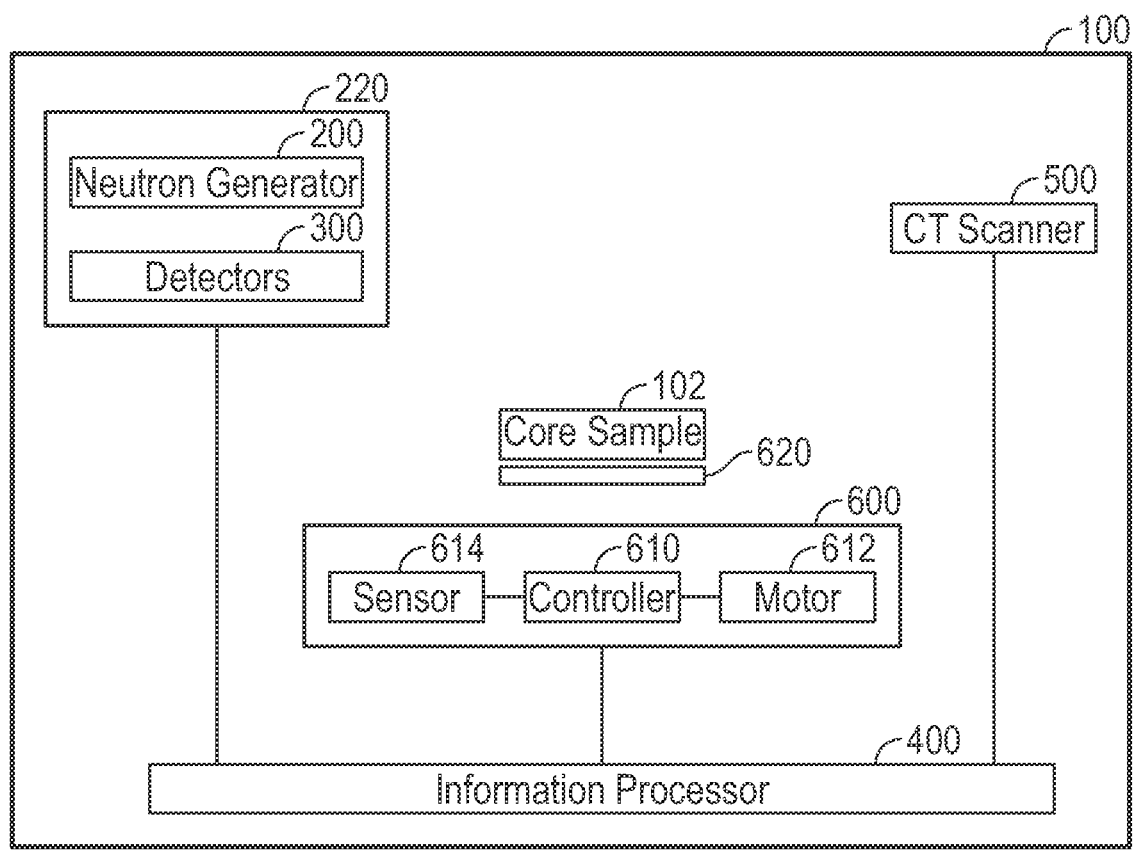
FIG. 1 schematically illustrates a system to analyze core samples according to one embodiment of the present disclosure.

Referring to FIG. 1, there is shown in block diagram format a non-limiting embodiment of a system 100 for analyzing a core sample 102 obtained from a subterranean formation. The system 100 may include a neutron generator 200 and a plurality of detectors 300, an information processor 400, and a transport system 600 that allows the core sample to be scanned along its long axis. The neutron generator 200 and the plurality of detectors 300 may be collectively referred to as the pulsed neutron apparatus 220. The system 100 also includes a computed tomography scanner 500. While FIG. 1 illustrates the pulsed neutron apparatus 220 and the computed tomography scanner 500 as co-located and in signal communication with the same information processor 400, the pulsed neutron apparatus 220 and the computed tomography scanner 500 may be structurally and functionally independent. However, it should be appreciated that correlating data provided by the pulsed neutron apparatus 220 to the data provided by the computed tomography scanner 500 will be most optimal if there is precise control and recording of linear position of the core sample 102 during analysis by each of these devices.

Figure 2:
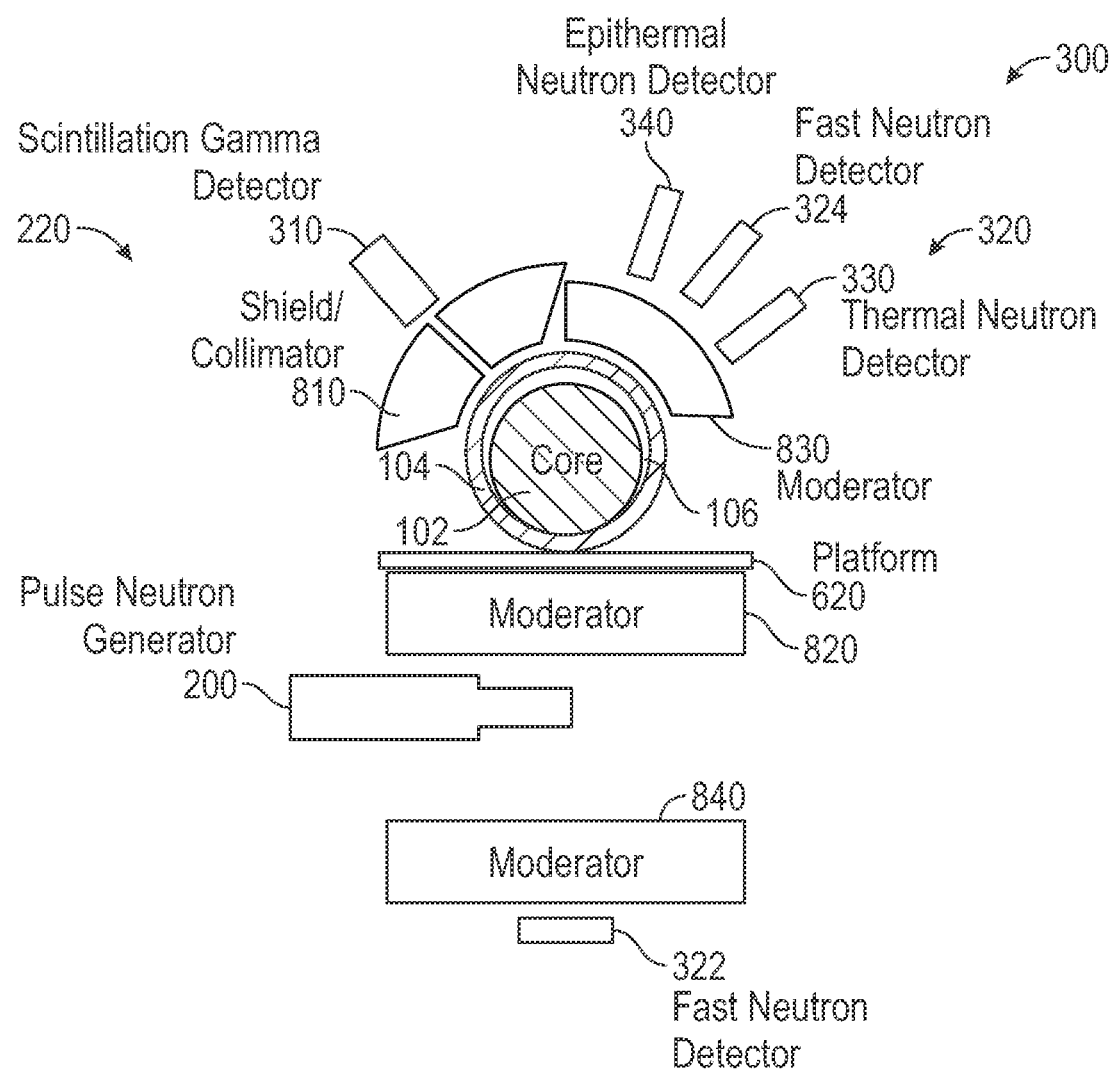
FIG. 2 schematically illustrates a pulsed neutron apparatus according to one embodiment of the present disclosure.

Referring to FIG. 2, there is shown one non-limiting embodiment of the pulsed neutron apparatus 220 according to the present disclosure. As discussed below, the pulsed neutron apparatus 220 may be used to perform a variety of measurements on the core sample 102 as a function of linear distance and by generating multiple different count rates.

The neutron generator 200 may be configured to operate in a pulsed mode and emit neutrons into the core sample 102. The neutrons may include fast neutrons. In certain embodiments, the neutron generator is a deuterium-tritium neutron generator that emits $10^7$ or more 14.1 MeV neutrons per second. Additionally, the neutron generator may have a frequency ranging from 10 to $10^6$ cycles per second, and a duty cycle ranging from 5% to 100%.

The plurality of detectors 300 may include at least one gamma detector 310, a plurality of fast neutron detectors 320, at least one thermal neutron detector 330, and at least one epithermal neutron detector 340.

The gamma detector 310 may be configured to estimate a gamma pulse-height spectrum that results from emitted neutrons interacting with the core sample 102. In embodiments, the gamma detector may include a scintillator coupled to a fast photomultiplier tube or a high-purity germanium semiconductor detector.

The fast neutron detectors 320 may be configured to generate two or more count rates. In one arrangement, the fast neutron detectors 320 may include at least: (i) a first fast neutron detector 322 configured to generate a count rate by monitoring the neutron generator output and counting the number of fast neutrons coming from the neutron generator 200 over a period of time, and (ii) a second fast neutron detector 324 configured to generate another count rate by counting the number of fast neutrons that are transmitted through the core sample 102 over the period of time. The first fast neutron detector 322 may include a scintillator coupled to a fast photomultiplier tube or a diamond detector. Likewise, the second fast neutron detector 324 may include a scintillator coupled to a fast photomultiplier tube or a diamond detector.

The thermal neutron detector 330 may be configured to generate a count rate by counting a number of thermal neutrons over the period of time. These thermal neutrons are emitted neutrons that have been slowed down to thermal energies by passing through the core sample 102. In one arrangement, the thermal neutron detector 330 includes a scintillator coupled to a photomultiplier tube, a $^3$He or $^{10}$B gas discharge tube, or a $^6$Li glass coupled to a photomultiplier tube.

The epithermal neutron detector 340 may be configured to generate a count rate by counting a number of epithermal neutrons over the period of time. These epithermal neutrons are emitted neutrons that have been slowed down to epithermal energies by passing through the core sample 102 but still have more energy than thermal neutrons. In one arrangement, the epithermal neutron detector 340 may be wrapped in Cd or a similar material.

Referring to FIG. 1, the computed tomography scanner 500 may be configured to aim a conical beam of X-rays at the core sample 102, which may be rotated around the core sample 102. The computed tomography scanner 500 may be configured to provide a radial and longitudinal estimate of the density of the core sample, and estimate the Pe of the core sample. The information generated by the computed tomography scanner 500 may be used to provide an image of the interior of a core barrel, along with estimates of the volumes of sample and fluid within the barrel (FIG. 4) in order to provide more precise data to go along with the neutron measurements.

The information processing device 400 is in signal communication with the detectors 300, and configured to separate count events on a nanosecond time scale. The information processing device 400 may be a conventional processor that includes microprocessors, memory modules programmed with suitable algorithms, input devices, etc.

Figure 3A:
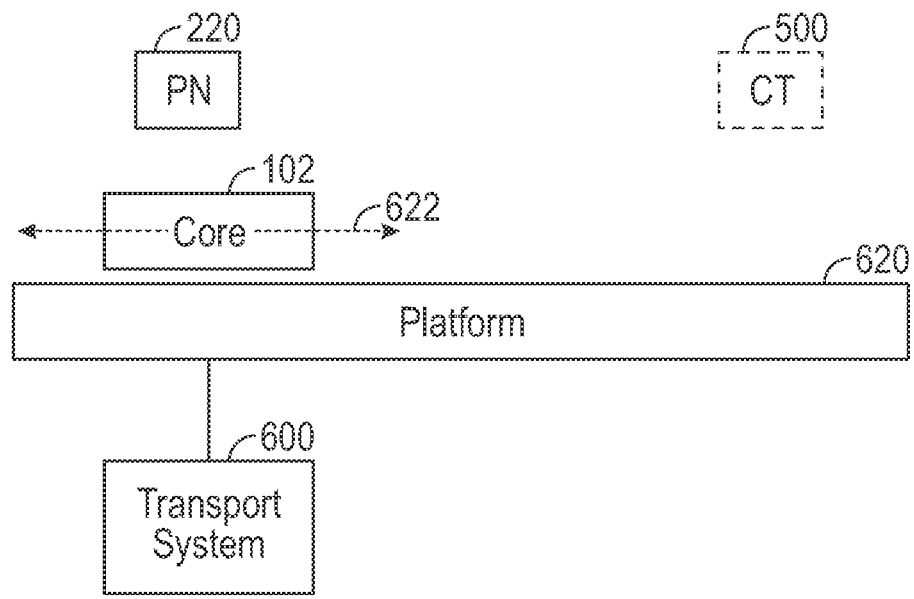
FIGS. 3A and 3B schematically illustrates transport systems according to embodiments of the present disclosure.
Figure 3B:
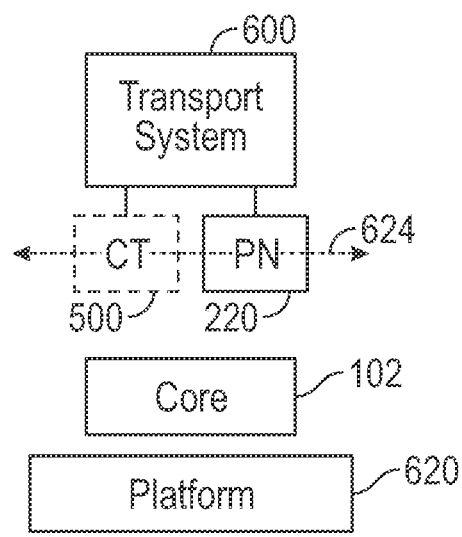

Referring to FIGS. 3A and 3B, the transport system 600 may be configured to allow relative movement between the core sample 102 and pulsed neutron apparatus 220. The transport system 600 may be configured to permit measurements to be made along the length of the core sample 102 by either continuous or discrete interval operating modes. The transport system 600 includes a controller 610 (FIG. 1), a motor 612 (FIG. 1), and one or more sensors 614 (FIG. 1). The controller 610 may be a microprocessor programmed with suitable algorithms to control the motor 6122 using measurements generated by the sensor 614 to ensure accurate alignment between pulsed neutron apparatus 220 and the computed tomography scanner 500 and the core sample 102. The transport system 600 may further include a platform 620 translated using the motor 612. Referring to FIG. 3A, the platform 620 may be configured to receive the core sample 102. In such embodiments, the pulsed neutron apparatus 220 and the computed tomography scanner 500 are stationary and the core sample 102 is moved linearly using the transport system 600 connected to the platform 620 as shown with dashed line 622. Referring to FIG. 3B, in other embodiments, the transport system 600 may be configured to support the pulsed neutron apparatus 220 and the computed tomography scanner 500. In such embodiments, the pulsed neutron apparatus 220 and the computed tomography scanner 500 are moved linearly using the transport system 600 as shown with dashed line 624 while the core sample 102 is stationary.

In embodiments where the pulsed neutron apparatus 220 and the computed tomography scanner 500 are co-located, the transport system 600 may include a translation assembly that precisely controls the linear position of the core sample 102 relative to the pulsed neutron apparatus 220 and the computed tomography scanner 500. If the pulsed neutron apparatus 220 and the computed tomography scanner 500 are not co-located, then a separate transport system 600 may be used for each apparatus.

In some embodiments, the system 100 may also include other features and enhancements, some of which are described below.

Referring to FIG. 2, in variants, a shielded collimator 810 may be located between the core sample 102 and the gamma detector 310. The shielded collimator 810 may be configured to restrict gamma measurement to a selected region of the core sample 102.

In further variants, the system 100 may include a first moderator 820 located between the neutron generator 200 and the core sample 102. The first moderator 820 may be configured to perform one or more functions such as to slow a fraction of the high-energy neutrons emitted by the neutron generator 200, and to scatter a fraction of the high-energy neutrons emitted by the neutron generator 200. In a related variant, a second moderator 830 may be located between the core sample 102 and the detectors 300. A third moderator 840 may be located between the neutron generator 200 and the fast neutron monitor 322.

Figure 4A:
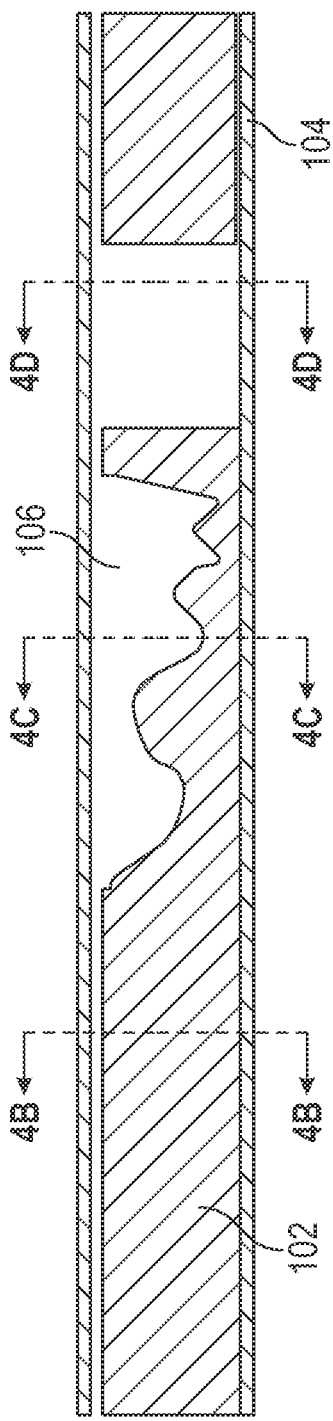
FIGS. 4A-D schematically illustrates an encapsulated core sample that may be analyzed using a system according to embodiments of the present disclosure.

FIG. 4A illustrates a sectional side view of a core sample 102 inside a core barrel 104. The inner core barrel 104 may be used to encapsulate and hermetically seal the core sample 102 along with a surrounding fluid 106. In such an arrangement, the neutron generator 200 (FIG. 1) may be configured to emit the neutrons through the inner core barrel 104. The detectors 300 (FIG. 1) in such an arrangement detect fast neutrons, thermal neutrons, epithermal neutrons that have passed through the inner core barrel 104, and emitted gamma rays resulting from neutrons interacting with the core sample 102.

Figure 4B:
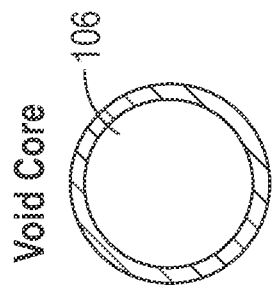
Figure 4C:
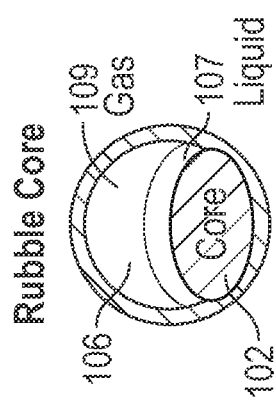
Figure 4D:
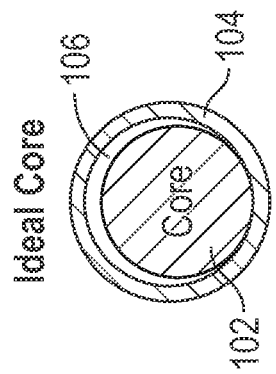

Referring to FIGS. 4B-D, the core sample 102 may not have a uniform shape or even have physical continuity. A section shown in FIG. 4B depicts a desirable cross-section wherein the core sample 102 is cohesive and generally resembles the cross-sectional shape when taken from the formation. A section shown in FIG. 4C depicts a cross-section wherein the core sample 102 has physically broken up and may be "rubble," i.e., composed of bits and pieces. As shown, the "rubble" may be surrounded by a fluid 106, which, as shown in FIG. 4C, can include liquid(s) 107 and gas(es) 109. A section shown in FIG. 4D depicts a cross-section in which there is a gap or complete physical discontinuity in the core sample 102. Thus, only the fluid 106 is present and there is no meaningful amount of any portion of the core sample 102 (FIG. 4A) in the cross-section of FIG. 4D.

Figure 5:
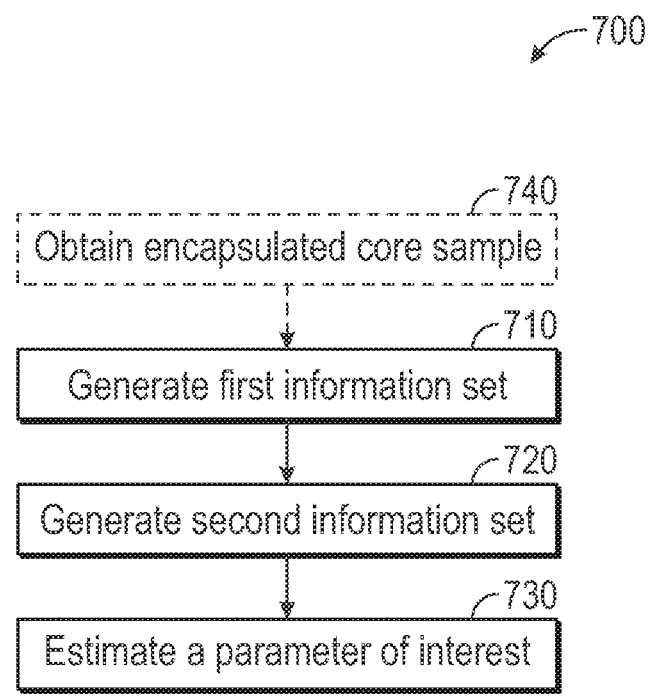
FIG. 5 is a flow chart illustrating one method of analyzing core samples according to one embodiment of the present disclosure.

Referring to FIG. 5, there is shown a flow chart illustrating a method 700 for analyzing a core sample obtained from a subterranean formation using the FIG. 1 system 100. Generally, the method 700 includes a step 710 of generating a first information set that includes neutron count rates, a step 720 of generating a second information set that includes measurements taken by the CT scanner 500 (FIG. 1), and a step 730 of estimating a selected parameter of interest relating to the subterranean formation from which the core sample 102 (FIG. 1) was taken by using the first information set and the second information set.

Referring to FIGS. 1 and 5, the step 710 may be performed by using the neutron generator 200 and the detectors 300 of system 100. The core sample 102, which may or may not be encapsulated, is first positioned on the platform 620.

The natural gamma spectrum may be measured with the neutron generator 200 turned off in order to obtain K, Th, and U concentrations of the core sample 102. These concentrations are commonly used to infer formation lithology and clay typing, and also to do bed matching of core samples in the current well and in neighboring wells.

Gamma spectra are also measured with the pulsed neutron generator 200 turned on and by using a variety of different pulse sequences. These pulse sequences generate associated count rates, which are composed of count events over a period of time. With a pulse sequence that emphasizes inelastic neutron scattering, gamma spectral peaks provide a C:O ratio for use in computing oil saturation, and also C, O, Al, Ca, Fe, Mg, Si, S, and Ti concentrations for elemental and mineral analysis of the core. With a neutron pulse sequence that emphasizes capture gamma rays, the gamma spectral peaks provide a considerable number of elemental concentrations that can be used to determine core sample mineralogy and also salinity of the core formation fluid. With a neutron pulse sequence that emphasizes build up and decay of the integrated gamma spectrum, the neutron capture cross section (Sigma) of the sample is measured. Simultaneously, thermal, epithermal, and fast neutron count rates can be used to determine the neutron porosity of core sample.

Thus, the first information set may include at least the first count rate generated by the first fast neutron detector 322, the second count rate generated by the second fast neutron detector 324, the third count rate generated by the thermal neutron detector 330, the fourth count rate generated by the epithermal neutron detector 340, and the fifth count rate (spectrum) generated by the gamma detector 310.

The step 720 may be performed by analyzing the core sample 102 using the computerized tomography scanner 500. The computerized tomography scanner 500 may be a conventional CT scanner configured to take a series of X-ray images from different angles around the core sample 102 and process the images to create cross-sectional images of the core sample 102.

It should be noted that steps 710 and 720 can be performed in any order or simultaneously.

At step 730, a variety of parameters of interest relating to the subterranean formation from which the core sample 102 may be estimated using the information obtained in steps 710 and 720.

For example, step 730 may include using the second information set to estimate at least one property of the core sample selected from one of: (i) density, (ii) Pe, and (iii) volume; and using the estimated at least one property to identify for the core sample at least one of: (i) a lithology and (ii) mineralogical composition.

Alternatively or additionally, step 730 may include estimating a neutron porosity of the core sample using the first information set. The first information set may include at least the first count rate generated by the first fast neutron detector 322, the second count rate generated by the second fast neutron detector 320, the third count rate generated by the thermal neutron detector 330, the fourth count rate generated by the epithermal neutron detector 340, and the fifth count rate (spectrum) generated by the gamma detector 310.

Alternatively or additionally, step 730 may be used to estimate neutron porosity. For example, the method may include the step of estimating the neutron porosity by also using an estimated value of a property of the core sample 102. The property may be one or more of density, Pe, and volume. Alternatively, or additionally, the method 700 may include the step of estimating the neutron porosity by also using one or more of: (i) an estimated lithology of the core sample, (ii) geometry and position of the core sample within the inner barrel, (iii) type and location of drilling fluid encased in the inner barrel, and (iv) salinity of fluid within pore spaces of the core sample.

Alternatively or additionally, step 730 may include the steps of estimating water saturation of the core sample by using the estimated neutron porosity and/or estimating hydrocarbon saturation of the core sample from a measurement of a ratio of carbon and oxygen yields in the subterranean formation, an estimated core sample porosity, and core sample lithology.

In embodiments, the method 700 may include a step 740 of using an inner core barrel 104 (FIG. 2) to encapsulate and hermetically seal the core sample 102 (FIG. 2). As noted above, in such an embodiment, the neutron generator 200 emits the neutrons through the inner core barrel 104 and the detectors 300 detect fast neutrons, thermal neutrons, epithermal neutrons that have passed through an inner core barrel 104, and emitted gamma rays resulting from neutrons interacting with the core sample 102.

By using the transport system 600 (FIG. 2), the method 700 may be performed on a cross-section by cross-section basis as the core sample 102 moves linearly relative to the pulsed neutron apparatus 220 and the computed tomography scanner 500. For each cross-section, the pulsed neutron apparatus 220 and the computed tomography scanner 500 each generate information that can be combined to accurately characterize each cross-section. Referring to FIGS. 4A-D, it should be appreciated that an analysis that analyzes separate cross-sections of a core sample can be corrected appropriately (a) for non-ideal core geometries (FIG. 4C and FIG. 4D), (b) for core density variability, and (c) for variable drilling mud volume.

What is claimed is:

1. An apparatus for analyzing a core sample obtained from a subterranean formation, comprising:
    (a) a neutron generator configured to operate in a pulsed mode and emit neutrons into the core sample, the neutrons including fast neutrons;
    (b) a plurality of detectors that includes:
        at least one gamma detector configured to estimate a gamma pulse-height spectrum that results from emitted neutrons interacting with the core sample,
        a plurality of fast neutron detectors generating at least a first count rate and a second count rate, the plurality of fast neutrons including at least: (i) first fast neutron detector configured to generate the first count rate by monitoring the neutron generator output and counting the number of fast neutrons coming from the neutron generator over a period of time, and (ii) a second fast neutron detector configured to generate the second count rate by counting the number of fast neutrons that are transmitted through the core sample over the period of time,
        at least one thermal neutron detector configured to generate a third count rate by counting a number of thermal neutrons over the period of time, the thermal neutrons being emitted neutrons that have been slowed down to thermal energies by passing through the core sample, and
        at least one epithermal neutron detector configured to generate a fourth count rate by counting a number of epithermal neutrons over the period of time, the epithermal neutrons being emitted neutrons that have been slowed down to epithermal energies by passing through the core sample but still have more energy than thermal neutrons;

(c) a computed tomography scanner in which a conical beam of X-rays is aimed at the sample and an opposing detector, both of which may be rotated around the sample;
    (d) an information processing device in signal communication with the plurality of detectors and configured to separate count events on a nanosecond time scale; and
    (e) a transport system configured to allow relative movement between the core sample and the plurality of detectors and between the core sample and the neutron generator.

2. The apparatus of claim 1, wherein the neutron generator is a deuterium-tritium neutron generator that emits $10^7$ or more 14.1 MeV neutrons per second, and wherein the neutron generator has a frequency ranging from 10 to $10^6$ cycles per second, and a duty cycle ranging from 5% to 100%.

3. The apparatus of claim 1, wherein the at least one gamma detector includes one of: (i) a scintillator coupled to fast photomultiplier tube, and (ii) a high-purity germanium semiconductor detector.

4. The apparatus of claim 1, further comprising a shielded collimator located between the core sample and the at least one gamma detector, the shielded collimator configured to restrict gamma measurement to a selected region of the core sample.

5. The apparatus of claim 1, wherein the first fast neutron detector and the second fast neutron detector include one of: (i) scintillator coupled to fast photomultiplier tube, and (ii) a diamond detector.

6. The apparatus of claim 1, wherein the at least one thermal neutron detector includes one of: (i) a scintillator coupled to a photomultiplier tube, (ii) a $^3$He or $^{10}$B gas discharge tube, and (iii) a $^6$Li glass coupled to a photomultiplier tube.

7. The apparatus of claim 1, wherein the at least one epithermal neutron detector, such as any of the thermal neutron counters mentioned above, which has been wrapped in Cd or a similar material.

8. The apparatus of claim 1, further comprising a first moderator located between the neutron generator and the core sample, the first moderator configured to at least one of: (i) slow a fraction of the high-energy neutrons emitted by the generator, and (ii) scatter the fraction of the high-energy neutrons emitted by the neutron generator.

9. The apparatus of claim 1, further comprising a second moderator located between the core sample and the plurality of detectors.

10. The apparatus of claim 1 wherein the transport system is further configured to permit measurements to be made along the length of the core sample by an operating mode selected from one of: (i) continuously, (ii) at discrete intervals.

11. The apparatus of claim 1, further comprising an inner core barrel in which the core sample is encapsulated and hermetically sealed, wherein the neutron generator is configured to emit the neutrons through the inner core barrel and wherein the plurality of detectors detect fast neutrons, thermal neutrons, epithermal neutrons that have passed through the inner core barrel, and gamma rays emitted by neutrons interacting with the core sample.

12. The apparatus of claim 1 where computed tomography is required to
    (a) provide a radial and longitudinal estimate of the density of the core sample,
    (b) and estimate the Pe of the core sample, (c) and provide an image of the interior of a core barrel, along with estimates of the volumes of core sample and fluid within the barrel.

13. A method for analyzing a core sample obtained from a subterranean formation, comprising:
 (a) generating a first information set by analyzing the core sample using the nuclear features (a) and (b) of claim 1;
 (b) generating a second information set by analyzing the core sample using the computerized tomography scanner feature of claim 1 (c); and
 (c) estimating a selected parameter of interest relating to the subterranean formation using the first information set and the second information set.

14. The method of claim 13, further comprising:
 using the second information set to estimate at least one property of the core sample selected from one of: (i) density, (ii) Pe, and (iii) volume; and
 using the estimated at least one properly to identify for the core sample at least one of: (i) a lithology and (ii) mineralogical composition.

15. The method of claim 13, further comprising: estimating a neutron porosity of the core sample using the first information set, the first information set including at least the first count rate, the second count rate, the third count rate, and the fourth count rate.

16. The method of claim 15, further comprising: estimating the neutron porosity by also using an estimated value of a property of the core sample, the property being at least one of: density, Pe, and volume.

17. The method of claim 15, further comprising estimating the neutron porosity by also using at least one of: (i) an estimated lithology of the core sample, (ii) geometry and position of the core sample within the inner barrel, (iii) type and location of drilling fluid encased in the inner barrel, and (iv) salinity of fluid within pore spaces of the core sample.

18. The method of claim 15, further comprising estimating water saturation of the core sample by using the estimated neutron porosity, the estimated capture cross section of the formation, and the capture cross sections of the pore-space fluids and the matrix.

19. The method of claim 15, further comprising estimating hydrocarbon saturation of the core sample from a measurement of a ratio of carbon and oxygen yields in the subterranean formation, an estimated core sample porosity, and core sample lithology.

20. The method of claim 13, further comprising: using an inner core barrel to encapsulate and hermetically seal the core sample, wherein the neutron generator is configured to emit the neutrons through the inner core barrel and wherein the plurality of detectors detect fast neutrons, thermal neutrons, epithermal neutrons that have passed through the inner core barrel, and gamma rays emitted from neutrons interacting with the core sample.

* * * * *